(12) United States Patent
Sournac et al.

(10) Patent No.: US 8,377,137 B2
(45) Date of Patent: Feb. 19, 2013

(54) INTERVERTEBRAL IMPLANT TO IMMOBILIZE ONE VERTEBRA RELATIVE TO ANOTHER

(75) Inventors: Denys Sournac, Reyrieux (FR); David Ryan, Collonges Au Mont d'Or (FR)

(73) Assignee: Medicrea International, Negron (FR)

( * ) Notice: Subject to any disclaimer, the term of this patent is extended or adjusted under 35 U.S.C. 154(b) by 379 days.

(21) Appl. No.: 12/741,228

(22) PCT Filed: Nov. 5, 2008

(86) PCT No.: PCT/IB2008/054603
§ 371 (c)(1),
(2), (4) Date: May 4, 2010

(87) PCT Pub. No.: WO2009/060387
PCT Pub. Date: May 14, 2009

(65) Prior Publication Data
US 2010/0262248 A1    Oct. 14, 2010

(30) Foreign Application Priority Data
Nov. 5, 2007 (FR) ........................... 07 07754

(51) Int. Cl.
*A61F 2/44* (2006.01)
*A61B 17/88* (2006.01)
(52) U.S. Cl. ..................... 623/17.16; 606/279
(58) Field of Classification Search .... 623/17.11–17.16; 606/60, 246–279, 280–299
See application file for complete search history.

(56) References Cited

U.S. PATENT DOCUMENTS

| | | | | |
|---|---|---|---|---|
| 5,609,635 A * | 3/1997 | Michelson | ................. | 623/17.16 |
| 6,200,347 B1 * | 3/2001 | Anderson et al. | .......... | 623/16.11 |
| 6,251,140 B1 * | 6/2001 | Marino et al. | ............. | 623/17.16 |
| 6,656,178 B1 * | 12/2003 | Veldhuizen et al. | .......... | 606/247 |
| 6,761,738 B1 * | 7/2004 | Boyd | ......................... | 623/17.11 |
| 7,601,173 B2 * | 10/2009 | Messerli et al. | ........... | 623/17.11 |
| 7,682,394 B2 * | 3/2010 | Recoules-Arche et al. | ........................ | 623/17.11 |
| 7,867,277 B1 * | 1/2011 | Tohmeh | ..................... | 623/17.11 |
| 8,157,845 B2 * | 4/2012 | Warnick et al. | .............. | 606/279 |
| 8,177,848 B2 * | 5/2012 | McKay | ..................... | 623/17.16 |
| 2004/0186572 A1 * | 9/2004 | Lange et al. | ............... | 623/17.11 |
| 2007/0016295 A1 | 1/2007 | Boyd | | |

FOREIGN PATENT DOCUMENTS
EP    1 731 116 A    12/2006

* cited by examiner

*Primary Examiner* — Kevin T Truong
*Assistant Examiner* — Christopher Beccia
(74) *Attorney, Agent, or Firm* — DeFillo & Associates, Inc; Evelyn A. Defillo

(57) ABSTRACT

This implant includes two elongated elements (1, 2) of reduced width, defining, at their edges, two longitudinal surfaces opposite each other. These elements (1, 2) being intended to be positioned between the vertebral plates (101) of the vertebrae, apart from each other, with their longitudinal surfaces in contact with the vertebral plates (101. Elements (1, 2) have curved shapes, having substantially the same curvature from one element (1, 2) to the other, and one of the elements (2) has a length smaller than that of the other element (1), the element (2) with the smaller length being intended to be placed in the anterior position on a vertebral plate (101) while the element (1) with the larger length is intended to be placed in the posterior position on this same vertebral plate (101).

7 Claims, 3 Drawing Sheets

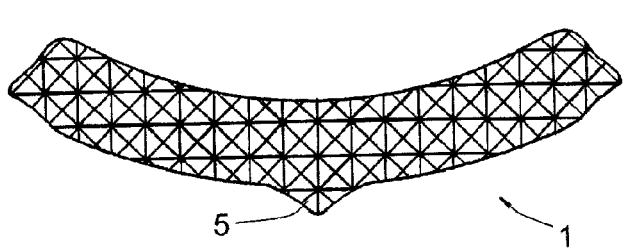
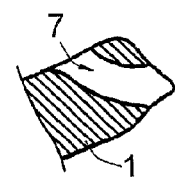
FIG. 1
FIG. 1A
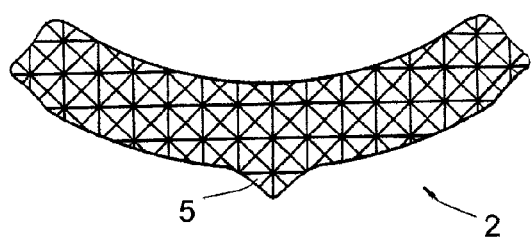
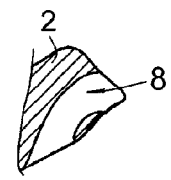
FIG. 2
FIG. 2A
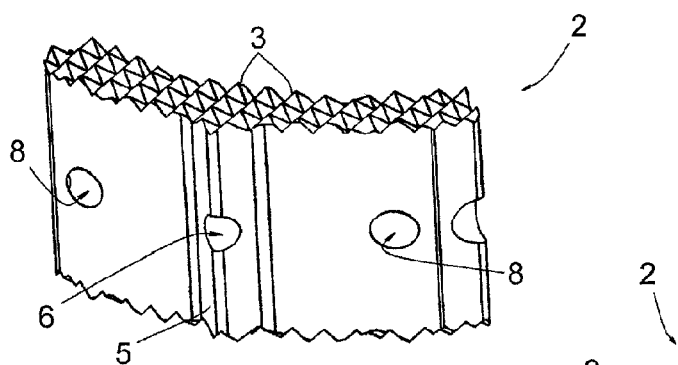
FIG. 3
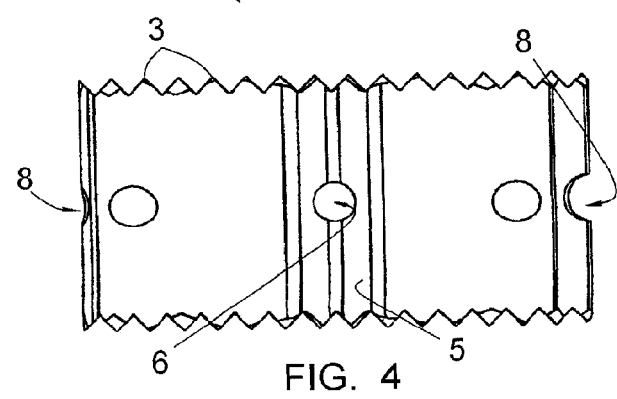
FIG. 4

INTERVERTEBRAL IMPLANT TO IMMOBILIZE ONE VERTEBRA RELATIVE TO ANOTHER

CROSS REFERENCE TO RELATED APPLICATION

This application is a national stage entry of PCT/IB2008/054603 filed Nov. 5, 2008, under the International Convention claiming priority over French Application No. 0707754 filed Nov. 5, 2007.

FIELD OF THE INVENTION

The present invention concerns an intervertebral implant making it possible to immobilize one vertebra relative to another.

The invention also relates to a surgical procedure with which a vertebra may be immobilized relatively to another.

BACKGROUND OF THE INVENTION

It is well known to immobilize two vertebrae relative to each other using an intervertebral implant in a rigid material, forming a cage which defines a housing, this housing being intended to receive one or several bone grafts and/or cancellous bone shavings. The implant makes it possible to reestablish suitable spacing of the vertebrae and to prevent crushing of the graft(s) by the said vertebrae. The vertebrae are immobilized relative to the implant by growth of bone cells through the graft(s) and/or shavings, leading to what is commonly called a "fusion" of two vertebrae.

Certain intervertebral implants have a reduced width, enabling their placement from the rear, on both sides of the spinal cord. It is then necessary to place two implants, one on the left side of the spinal cord and the other on the right side.

This technique has the drawbacks of being relatively risky to implement, involving the piercing of holes near the spinal cord, requiring the use of hollow implants with a reduced width, allowing only a small contact surface of the grafts with the vertebrae, and not being usable on spinal vertebrae, for reasons related to anatomy.

To resolve these drawbacks, it is common to place an intervertebral implant from the front. The approach being larger than from the rear, such an implant can have a shape such that it extends over a major part of the surface of the vertebral plate, and can therefore contain one or several grafts having a significant contact surface with the vertebral plates, which is an essential condition for the success of the vertebral fusion. An implant of this type comprises a peripheral wall defining said housing and one or several internal partitions making it possible to strengthen its structure so that it can bear the stresses exerted on it during its impaction between the vertebrae.

This type of implant, largely used in practice, is not, however, fully satisfactory with regard to the vertebral fusion obtained.

Document US 2007/016295 describes an implant comprising two elongated elements with a reduced width, defining, at the level of their edges, two longitudinal surfaces opposite each other, these elements being intended to be positioned between the vertebral plates of the vertebrae, away from each other, with their longitudinal surfaces in contact with the vertebral plates.

The shaping of these implants does not, however, make it possible to achieve the objectives of being able to be easily introduced into the intervertebral space, being able to be arranged optimally in this space and being able to be maintained in a suitable position in this space.

Documents U.S. Pat. No. 5,397,364, EP1752116A1 and U.S. Pat. No. 6,656,178 describe different types of implants which do not make it possible to resolve the aforementioned drawbacks.

SUMMARY OF THE INVENTION

The primary objective of the invention is therefore to resolve the drawbacks of the prior art, by providing an implant which can be easily introduced into the intervertebral space, able to be arranged optimally in this space and able to be kept in suitable position in this space.

Another objective of the invention is to provide an intervertebral implant which is simpler and less costly to manufacture than the existing implants.

The concerned implant comprises, in a known manner, two elongated elements of reduced width, defining, at their edges, two longitudinal surfaces opposite each other, these elements being intended to be positioned between the vertebral plates of the vertebrae, apart from each other, with their longitudinal surfaces in contact with the vertebral plates.

According to the invention, the elements have curved shapes, having substantially the same curvature from one element to the other, and one of the elements has a length smaller than that of the other element, the element with the smaller length being intended to be placed in the anterior position on a vertebral plate while the element with the larger length is intended to be placed in the posterior position on this same vertebral plate.

Thanks to their curved shape, of the same curvature from one element to the next, and their reduced width, these two elements occupy a reduced volume when they are placed one against the other; they can thus be introduced between the vertebrae simultaneously, via an approach of limited invasiveness, in particular through the lateral approach.

The two elements are then placed between the vertebral plates, then positioned apart from each other, the element with the smaller length being placed in the most anterior position possible and the element with the larger length being placed in the most posterior position possible.

The curvature of these elements thus allows them to be adapted to the patient's morphology as well as possible, and to obtain the greatest possible stability of the implant. It ensures maintenance of the elements in position relative to the vertebrae notwithstanding their reduced width (by reduced width, is designated a length generally smaller than 1 cm).

Once the elements are in place, one or several bone grafts and/or bone shavings can be placed between these elements. The latter parts ensure maintenance in position of this or these bone graft(s) and/or shavings.

Thus, the implant according to the invention does not comprise a peripheral wall or internal partitions, such that it makes it possible to obtain a large contact surface of one or several bone graft(s) and/or bone shavings with the bone plates. Moreover, this implant does not involve filling before insertion between the vertebrae or impaction, such that the risk of loss of grafts or bone shavings, or deterioration of these grafts or shavings, during placement of the implant, is eliminated.

The result is that the implant according to the invention makes it possible to obtain a fusion of vertebrae under the best possible conditions.

The two elements can have different heights, the element with the smaller length having a height greater than that of the element with the larger length.

The implant according to the invention has the additional advantage of making it possible to reduce the number of implants needed in a line of implants, given that the desired angle of curvature can be obtained through the combination of two elements of two different heights. On the contrary, according to the prior art, a standard line of implants comprises implants of different heights and, for an implant of a given height, several implants with different angles of curvature.

Preferably, the implant comprises connecting means making it possible to connect one element to the other.

These connecting means make it possible, by connecting the elements, to increase the stability of these elements relative to the vertebrae.

Advantageously, in this case, the connecting means comprise at least one connecting member formed to make it possible to bring one element closer to the other after placement.

This bringing closer makes it possible, after implantation, to compress the graft(s) and/or shavings placed between the elements so as to compress this or these graft(s) and/or shavings between these elements. This compression ensures the cohesion of the graft(s) and/or shavings as well as their good contact with the vertebral plates, which is totally favorable to obtaining a perfect bone fusion.

According to one embodiment of the invention, said connecting member comprises a connection able to be engaged around elements and to be tensioned so as to bring the elements closer together.

Preferably, in this case, at least one element comprises at least one hole for the passage of the connection through it.

The connection is thus guided in relation to the element, and can be connected to the element in order to be able to be inserted between the vertebrae at the same time as the latter part.

Advantageously, in this case, each element comprises two holes which go through it, near its ends, through which the connection is able to be engaged with the possibility of sliding, the holes of the two elements making it possible to guide the connection along these elements and to connect this connection to these elements.

The elements and the connection thus form a unitary assembly able to be inserted in a single operation. The positioning of the two elements one away from the other is then done by separating these elements from each other, this separation being made possible by the sliding of the connection through said holes.

According to another embodiment of the invention, said connection means comprise two rods able to connect the elements to each other, these rods being able to be immobilized relative to the elements in the close together position of these elements, in particular through crimping of blocking parts on their ends going through an element.

These rods can have a curved shape whereof the convex edges extend from the side opposite the space intended to be defined by the elements. These rods thus do not limit this space, intended to receive one or several bone graft(s) and/or bone shavings, which preserves large dimensions.

According to another embodiment of the invention, said connecting means comprise at least one screw making it possible, by its screwing, to bring one element closer to the other element.

At least one element can comprise asperities on at least one of its curved longitudinal surfaces, in particular in the form of series of dots of pyramidal shape or of ribs.

At least one element can moreover comprise at least one rib protruding from at least one of its curved surfaces.

This rib locally increases the width of an element and favors the stability thereof in relation to the vertebrae.

The two elements of the implant according to the invention can be put into place using any prospective approach, rear, lateral or front, or by any approach combining these directions, in particular by a posterolateral path.

When the elements are intended to be placed via a front approach, each element comprises a median transverse hole allowing its connection to an insertion and/or impaction instrument.

The invention also relates to a surgical method for immobilizing a vertebra relatively to another one, comprising the steps consisting of:
using an intervertebral implant (1) according to any of claims 1 to 12;
introducing simultaneously the two elements that form this implant between the vertebral plates;
positioning these two elements apart from each other.

The method may comprise the step consisting, after placement of the two elements between the vertebrae, of placing one or several cancellous bone shavings between the elements.

The method may comprise the step consisting of placing bone graft(s) and/or cancellous bone shavings in excess between the elements.

The method may comprise the step consisting of:
using an intervertebral implant (1) according to any of claims 4 to 12;
after placement of bone graft(s) and/or cancellous bone shavings, acting on said connecting member for bringing the elements closer from each other, in order to achieve a compaction of this or these bone grafts and/or cancellous bone shavings between the elements.

BRIEF DESCRIPTION OF THE DRAWINGS

The invention will be well understood, and other characteristics and advantages thereof will appear, in reference to the appended diagrammatic drawing, illustrating, as non-limiting examples, several possible embodiments of the intervertebral implant it concerns.

FIG. 1 is a top view of a first element comprised by this implant;

FIG. 1A is a longitudinal cross-sectional view of the end of the element appearing on the right of FIG. 1;

FIG. 2 is a top view of a second element comprised by this implant;

FIG. 2A is a longitudinal cross-sectional view of the end of the element appearing on the right in FIG. 2;

FIG. 3 is a perspective view of the element of FIG. 2;

FIG. 4 is a front view;

For simplification, the parts or elements of one embodiment which are found identically or similarly in another embodiment will be identified by the same numerical references and will not be described again.

DETAILED DESCRIPTION OF THE INVENTION

FIGS. 1 and 2 illustrate two elongated elements 1, 2 jointly making it possible to form an intervertebral implant for immobilization of one vertebra relative to another.

Figure 6:
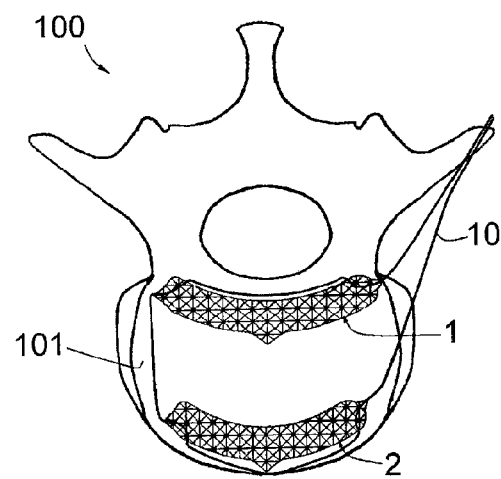
FIG. 6 is a view similar to FIG. 5, after placement of the elements between the vertebrae and before tightening of the connection.
Figure 7:
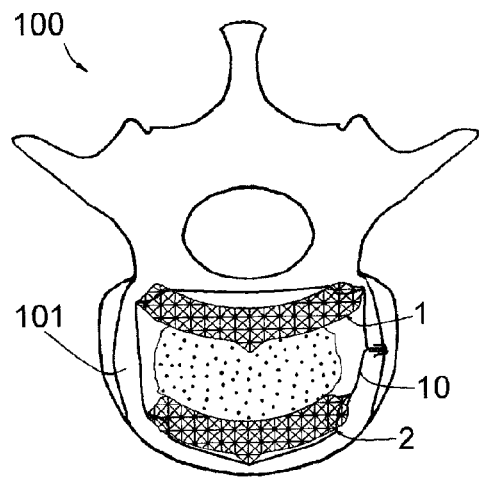
FIG. 7 is a view similar to FIG. 6, after placement of a graft between the elements and tightening of the link.
Figure 8:
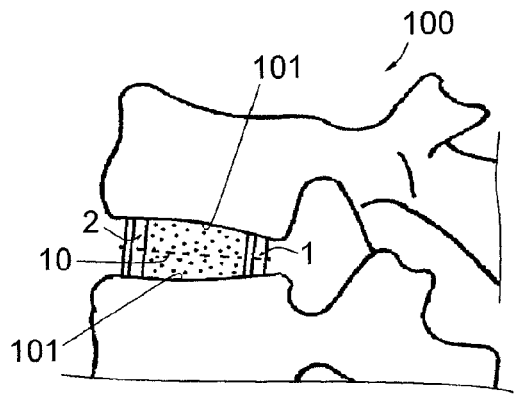
FIG. 8 is a side view of the two vertebrae, after placement of the implant.

As shown by FIGS. 6 to 8, the element 1 is intended to be placed from the posterior side of the vertebral plates 101 of two vertebrae 100. It has a length greater than that of the element 2, itself intended to be placed from the anterior side of these plates 101, and has a height smaller than that of said element 2. It appears in FIG. 8 that the respective heights of the elements 1 and 2 are such that these elements make it possible, once placed between the plates 101, to replace the vertebrae 100 in a position of anatomic curvature.

In reference again to FIGS. 1 to 4, it appears that each element 1, 2 has a curved shape and a reduced width, this width being less than 1 cm. At its edges, each element 1, 2 defines two curved longitudinal surfaces opposite each other, intended to come into contact with the plates 101, which each comprise a plurality of asperities 3 for bearing against these plates, in the form of pyramidal points.

Each element 1, 2 also comprises a median rib 5 protruding from its convex curved surface, pierced by a hole 6 allowing, in case of anterior approach, assembly of the element on an insertion and/or impaction instrument (not shown).

As shown more particularly in FIGS. 1A and 2A, and 3 and 4, the element 1 comprises two curved conduits 7 at its ends, leading, on one hand, into the longitudinal end surface of the element 1 and, on the other hand, into the concave surface of this element, i.e. into the surface thereof intended to be turned from the rear side after implantation. The element 2 itself comprises two curved conduits 8 at its ends, leading, on one hand, into the convex surface of the element 2, i.e. into the surface thereof intended to be turned from the anterior side after implantation, and, on the other hand, in the longitudinal end surface of this element.

Figure 5:
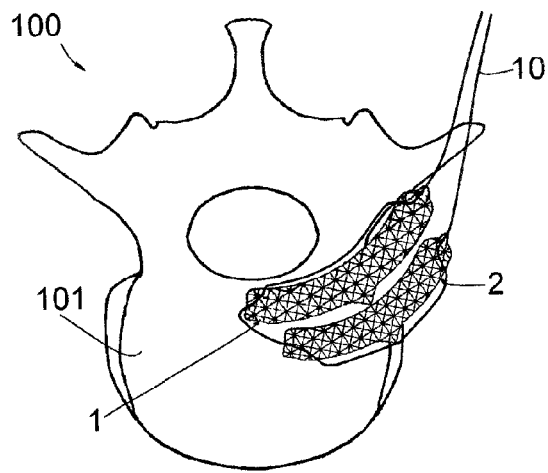
FIG. 5 is a top view of a vertebra, during the introduction between this vertebra and the superjacent vertebra of the implant formed by the two aforementioned elements and by a connection engaged around these elements.

It appears in FIGS. 5 to 7 that the conduits 7 and 8 of the two elements 1 and 2 are intended to be passed through by a connection 10 such that this connection bypasses these elements 1, 2.

In practice, in the illustrated example, the two elements 1, 2 are intended to be introduced posterolaterally (cf. FIG. 5), then being in their close together position, and to be placed between the vertebral plates 101 of the vertebrae 100, then to be positioned apart from each other (cf. FIG. 6), by sliding of the connection 10 in the conduits 7, 8. In this position, the curved shape of these elements 1, 2 ensures their maintenance in position relative to the vertebrae 100 notwithstanding their reduced width.

One or several bone grafts, and/or bone shavings, diagrammed by dots in FIGS. 7 and 8, can then be placed between the elements 1, 2, then traction can be exerted on the connection 10 in order to bring these two elements closer to each other, thereby putting the bone graft(s) and/or bone shavings in compression.

The connection 10 can then be tied or twisted so as to maintain this close together position of the elements 1, 2, then its end strands can be cut at the knot or twist.

As understood, the implant according to the invention does not comprise a peripheral wall or internal partitions, such that it makes it possible to obtain a large contact surface of one or several bone grafts and/or bone shavings with the vertebral plates 101. Moreover, this implant does not involve filling before insertion between the vertebrae 100 nor impaction, such that the risk of losing bone grafts or shavings, or of deterioration of these grafts or shavings, during placement of the implant, is eliminated.

Moreover, the structure of the implant in two elements makes it possible for the implant to be best adapted to the morphology of the patient, by positioning the element 2 in the most anterior position possible and the element 1 in the most posterior position possible. The greatest possible stability of the implant is thus obtained.

The implant according to the invention has the additional advantage of making it possible to reduce the number of implants needed in a line of implants, given that the desired angle of curvature can be obtained through the combination of two elements 1, 2 of different heights.

Figure 9:
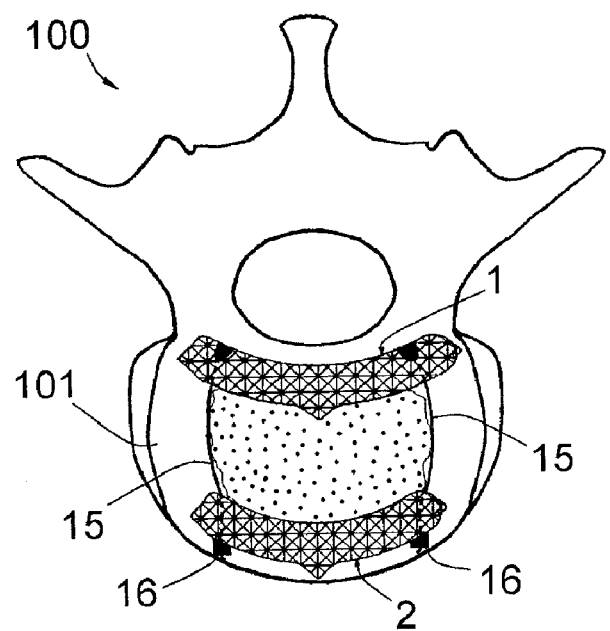
FIG. 9 is a view similar to FIG. 7 of the implant according to another embodiment.

FIG. 9 illustrates an implant formed by two elements 1, 2 similar to those described above but not comprising conduits 7, 8 as previously mentioned. Instead and in place, these elements 1, 2 comprise conduits going all the way through them, from their concave surface to their convex surface, and the implant comprises two rods 15 intended to connect the elements 1, 2 to each other.

Each rod 15 comprises a tip fixed at one of its ends, intended to bear against the rear surface of the element 1, and is intended to go through the conduit of the element 1, then the corresponding conduit of the element 2, and to receive a blocking piece 16 in a deformable material on its exceeding part on the anterior surface of the element 2, this piece 16 being intended to be crimped on said exceeding part so as to immobilize the two elements 1, 2 in relation to each other.

In practice, the element 1 is placed through the anterior approach with the rods 15 engaged through its conduits then, after placement of one or several grafts and/or shavings before this element 1, the element 2 is placed with insertion on the exceeding parts of the rods 15. The pieces 16 are then engaged on these exceeding parts and a traction is exerted on the rods 15 so as to bring the two elements 1, 2 closer together and to thus place the grafts and/or shavings in compression between these two elements. Said exceeding parts of the rods 15 are then cut at the level of the pieces 16.

As illustrated, the rods 15 can have a curved shape whereof the convex edges extend from the side opposite the space defined by the elements 1, 2. The rods 15 thus do not limit this space, which keeps large dimensions.

Figure 10:
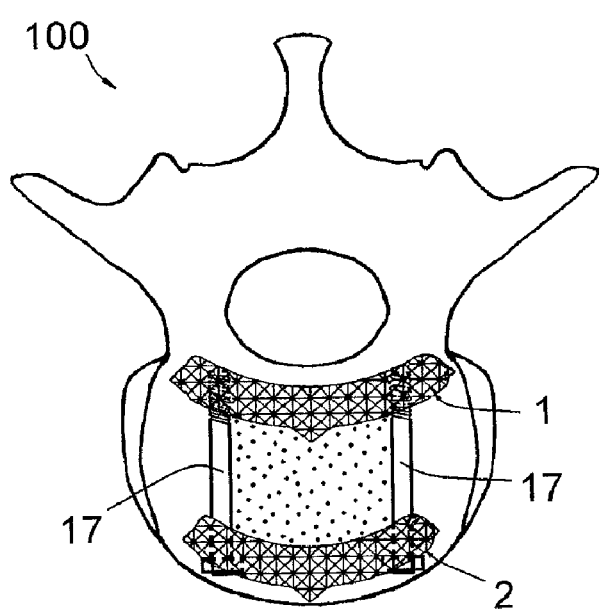
FIG. 10 is a view similar to FIG. 7 of the implant according to yet another embodiment.

FIG. 10 also shows another embodiment of the implant according to the invention, of structure similar to that described above but comprising screws 17 instead and in place of the rods 15. The conduits of the element 1 can then be threaded to receive these screws 17 by screwing, which comprise heads bearing against the anterior surface of the element 2, assuming position in the counterbores arranged in this anterior surface. According to another possibility, in this case, the implant comprises threaded rods screwed into the conduits of the element 1, which receive nuts on their parts exceeding beyond the anterior surface of the element 2.

As appears from the preceding, the invention provides an intervertebral implant making it possible to immobilize one vertebra in relation to another, which presents many advantages relative to similar implants of the prior art, in particular those making it possible to obtain a fusion of vertebrae under the best possible conditions, having a reduced production cost, allowing a number of different approaches and being able to be easily and quickly adapted to the patient's morphology.

The invention was described above in reference to embodiments provided purely as examples. It goes without saying that it extends to all embodiments covered by the appended claims. In particular, the grafts and shavings can be natural or synthetic.

The invention claimed is:

1. An intervertebral implant to immobilize one vertebra relative to another comprising:
    two elongated elements of reduced width, defining, at their edges, two longitudinal surfaces opposite each other, wherein the elongated elements are positioned between vertebral plates of the vertebrate, apart from each other, with their longitudinal surfaces in contact with the vertebral plates;
    wherein the elongated elements have curved shapes, having the same curvature from one elongated element to the other elongated element, and one of the elongated elements has a length smaller than that of the other elongated element, the elongated element with the smaller length being intended to be placed in an anterior position on one of the vertebral plate while the elongated element with the larger length is intended to be placed in the posterior position on this same vertebral plate;
    the implant comprises connecting devices to connect one of the elongated elements to the other elongated element;
    the connecting devices comprise at least one connecting member to bring one of the elongated elements closer to the other elongated members after placement; and
    the connecting member comprises a connection element, the connection element is tied or twisted around the elongated elements, the connection element is able to be tensioned to bring the elongated elements closer together, the connection element including ends that are cut at the knot or twisted.

2. The intervertebral implant according to claim 1, wherein the two elongated elements have different heights, the elongated element with the smaller length having a height greater than that of the elongated element (1) with the larger length.

3. The intervertebral implant according to claim 1, wherein at least one of the elongated elements comprises at least one hole for the passage of the connection element through it.

4. An intervertebral implant to immobilize one vertebra relative to another comprising:
    two elongated elements of reduced width, defining, at their edges, two longitudinal surfaces opposite each other, wherein the elongated elements are positioned between vertebral plates of the vertebrate, apart from each other, with their longitudinal surfaces in contact with the vertebral plates;
    wherein the elongated elements have curved shapes, having the same curvature from one elongated element to the other elongated element, and one of the elongated elements has a length smaller than that of the other elongated element, the elongated element with the smaller length being intended to be placed in an anterior position on one of the vertebral plate while the elongated element with the larger length is intended to be placed in the posterior position on this same vertebral plate;
    the implant comprises connecting devices to connect one of the elongated elements to the other elongated element;
    the connecting devices comprise at least one connecting member to bring one of the elongated elements closer to the other elongated members after placement;
    the connecting member comprises a connection element, the connection element is tied or twisted around the elongated elements, the connection element is able to be tensioned to bring the elongated elements closer together, the connection element including ends that are cut at the knot or twisted;
    each one of the elongated elements comprises a hole on each end, a first end of the connection element passes through the holes of one of the elongated elements and then through the holes of the other elongated element and then is secured to a second end of the connection element.

5. The intervertebral implant according to claim 1 wherein at least one of the elongated elements comprises asperities on at least one of its curved longitudinal surfaces, the asperities are in a form of series of dots of pyramidal shape or of ribs.

6. The intervertebral implant according to claim 1 wherein one of the elongated elements comprises at least one rib protruding from at least one of its curved surfaces.

7. An intervertebral implant to immobilize one vertebra relative to another comprising:
    two elongated elements of reduced width, defining, at their edges, two longitudinal surfaces opposite each other, wherein the elongated elements are positioned between vertebral plates of the vertebrate, apart from each other, with their longitudinal surfaces in contact with the vertebral plates;
    wherein the elongated elements have curved shapes, having the same curvature from one elongated element to the other elongated element, and one of the elongated elements has a length smaller than that of the other elongated element, the elongated element with the smaller length being intended to be placed in an anterior position on one of the vertebral plate while the elongated element with the larger length is intended to be placed in the posterior position on this same vertebral plate;
    the implant comprises connecting devices to connect one of the elongated elements to the other elongated element;
    the connecting devices comprise at least one connecting member to bring one of the elongated elements closer to the other elongated members after placement, the connecting element is a cord;
    the connecting member comprises a connection element, the connection element is tied or twisted around the elongated elements, the connection element is able to be tensioned to bring the elongated elements closer together, the connection element including ends that are cut at the knot or twisted;
    each one of the elongated elements comprises a hole on each end, a first end of the connection element passes through the holes of one of the elongated elements and then through the holes of the other elongated element and then is secured to a second end of the connection element.

* * * * *